United States Patent [19]
Muto

[11] 4,392,853
[45] Jul. 12, 1983

[54] STERILE ASSEMBLY FOR PROTECTING AND FASTENING AN INDWELLING DEVICE

[76] Inventor: Rudolph Muto, 24 Williams St., Andover, Mass. 01810

[21] Appl. No.: 244,000

[22] Filed: Mar. 16, 1981

[51] Int. Cl.³ .................... A61M 5/00; A61M 25/02
[52] U.S. Cl. .................................. 604/171; 604/174; 604/180; 128/DIG. 26
[58] Field of Search .............. 128/348, 349, 350, 214, 128/214.4, DIG. 26; 604/163, 171, 174, 180, DIG. 26

[56] References Cited

U.S. PATENT DOCUMENTS

| | | | |
|---|---|---|---|
| 3,683,911 | 8/1972 | McCormick | 128/348 |
| 3,853,130 | 12/1974 | Sheridan | 128/DIG. 26 |
| 3,856,020 | 12/1974 | Kovac | 128/DIG. 26 |
| 4,051,849 | 10/1977 | Poncy et al. | 128/348 X |
| 4,327,723 | 5/1982 | Frankhouser | 128/214.4 |
| 4,327,735 | 5/1982 | Hampson | 128/348 |

*Primary Examiner*—Stephen C. Pellegrino
*Attorney, Agent, or Firm*—Pearson & Pearson

[57] ABSTRACT

A sterile assembly and method for protecting and affixing an indwelling device such as an elongated catheter, or pacer lead, in an incision in the human body includes an elongated, hollow tubular, sheath of transparent, relatively limp, impervious plastic having at its proximal end a dome of self-supporting plastic adherable around the incision and having, at its distal end, an elongated tube, several inches in length, of self-supporting plastic. The sheath is shipped accordion folded onto the tube to save space. The indwelling device is sleeved into the sheath with the conventional nub at its distal end wedged in the bore. The proximal end is introduced into the incision and the domed distal end of the sheath is adhered around the incision so that the device is contamination free. The device and sheath are then gripped in the slot of a clamp and the clamp adhered to the body near the incision or elsewhere. The Introducer may be withdrawn into the sheath away from the incision, while remaining sealed in the sheath.

11 Claims, 12 Drawing Figures

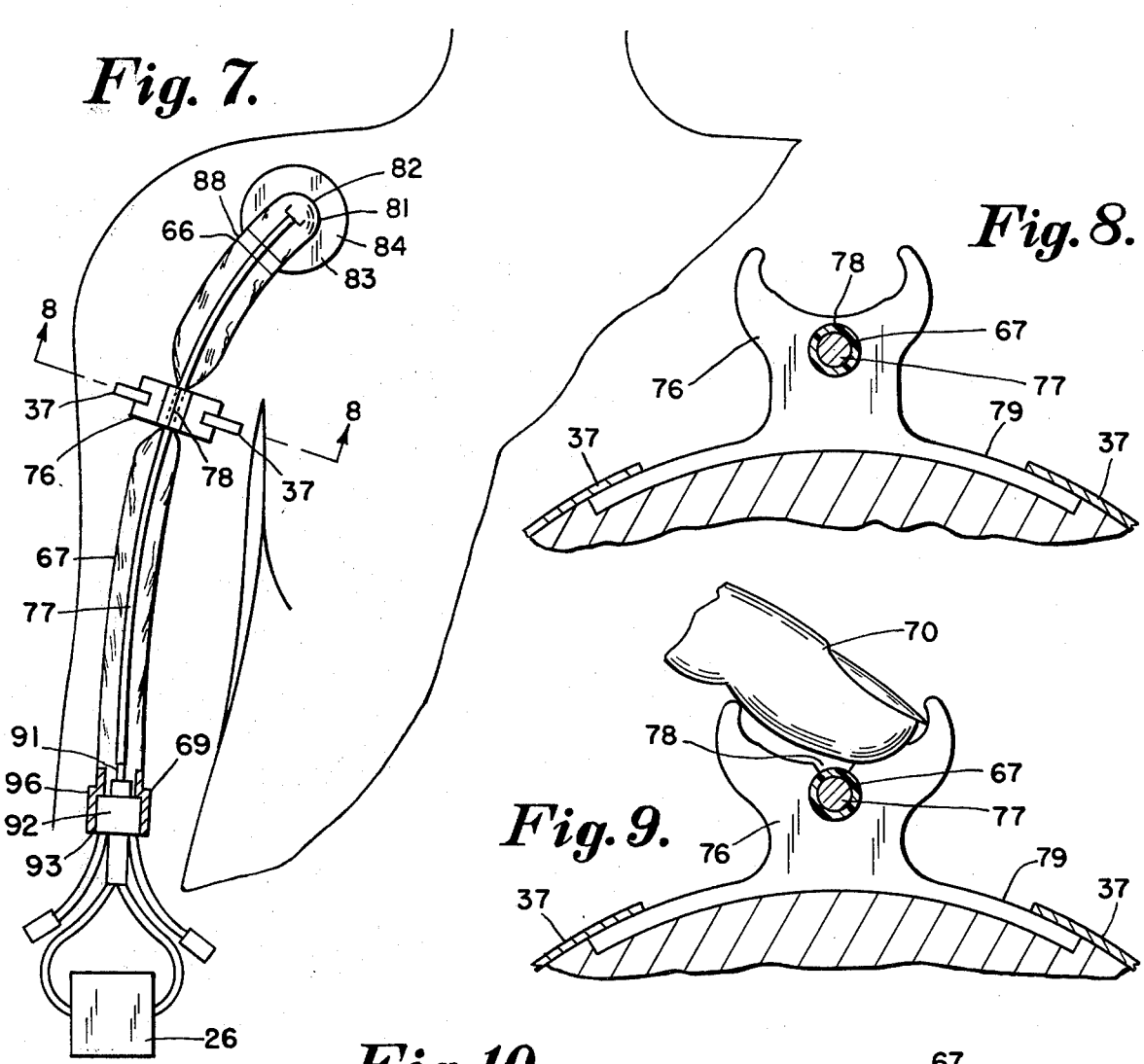

STERILE ASSEMBLY FOR PROTECTING AND FASTENING AN INDWELLING DEVICE

BACKGROUND OF THE INVENTION

There have been a number of patents granted on retaining devices for catheters, flexible tubes or leads which are inserted in incisions in the human body, the devices being of the flexible strip type usually with plastic foam encircling the tube and the tape, or strip, folded around the tube and tied or taped to the limb or body. Exemplary of such devices are U.S. Pat. No. 2,669,231 of Feb. 16, 1954 to Fisher, U.S. Pat. No. 3,726,280 of Apr. 10, 1973 to LeCount and U.S. Pat. No. 4,088,136 of May 9, 1978 to Hasslinger, et al. These anchoring devices must usually be untied, or unfastened, before the catheter or tube can be manipulated for advance or retraction and the fold over requirement makes them difficult to emplace.

It has also been proposed to provide a catheter clamp in the form of a disc having a block thereon, the block having a central hole for a trocar and an elongated open slit for receiving and locking a length of a catheter which has been inserted in the hole. Such a clamp block is disclosed in U.S. Pat. No. 3,568,679 to Reif of Mar. 9, 1971 and it is characterized by the fact that the catheter slot in the block is the locking device which locks the catheter at a desired location, when the semi-rigid material of the block closes around the catheter.

In U.S. Pat. No. 3,853,130 to Sheridan of Dec. 10, 1974 a somewhat similar concept is disclosed, there being no locking block, or clamp, but the catheter being enclosed in a longitudinally split sheath which is shorter in length than the catheter. The open slit, or slot, is of diameter substantially equal to the diameter of the catheter. Thus, the catheter is normally locked against sliding movement in the sheath slot and while the ribs of the sheath can be pulled away from each other to strip the catheter and sheath away from each other, slidability is not achieved while the catheter is in the slot.

SUMMARY OF THE INVENTION

In one form of the catheter clamp of this invention, the clamp body includes an open slot which is normally of greater inner diameter than the outer diameter of the catheter so that a catheter in the slot can be slidably advanced or retracted freely until the tip within the human body is in the desired position. The clamp body also includes a pair of flared, arms each upstanding from a common central portion, on an opposite side of the slot, to constitute clamp jaws which are normally spaced from each other. The clamp body also includes a base flange by which the clamp can be adhered to the skin near an incision, or taped, tied or otherwise anchored.

A locking member, separate from the clamp body, but dimensioned to fit over the upstanding arms, or clamp jaws, and preferably in the form of a hollow, plastic sleeve, is provided to apply pressure to the clamp to reduce the diameter of the slot to lock a length of a catheter against slidable axial movement.

The locking member, or sleeve is of flexible, resilient material and so cooperates with the configuration of the clamp jaws, or arms, that gentle finger pressure thereon in the direction of the slot causes the slot to increase in diameter to enable the surgeon to advance or retract the catheter in the slot without having to remove it from the clamp.

Preferably the clamp block, or body, includes an integral, forward projecting, tapered nose, which includes an extension of the catheter slot in the clamp body and which fits in the tapered, female recess in the rear of a conventional trocar or introducer.

Preferably attached to the locking sleeve is an elongated, hollow tubular sheath of transparent thin, impermeable plastic having its proximal end sealed around the sleeve and its distal end closed around the distal end of the catheter, so that the catheter is completely covered and enclosed. Thus, the surgeon can manipulate and press the sleeve and clamp jaws, finger the catheter and otherwise make adjustments through the material of the sheath with all parts fully enclosed and without contaminating the parts of the clamp, sleeve, or catheter.

The tubular, full length sheath is attached to the outer end of the locking sleeve and clamp to prevent contamination by the fingers and preferably the inner end of the sleeve is provided with an inner wall to prevent cantamination of the catheter by the fingers of the surgeon during manipulation.

In another form of the invention the indwelling device, whether a solid elongated electrode, or an elongated, hollow catheter, is fully enclosed and covered by the hollow tubular sheath of thin wall, flexible plastic, the proximal end of the sheath having a bell shaped dome of clear, self-supporting plastic with an enlarged flange adhered around the incision and the distal end of the sheath being sealed around the distal end of the indwelling device. In this embodiment the clamp is exposed and may be attached to the skin of the patient at a spaced distance from the incision. The clamp slot is of such diameter as to normally grip both the length of the device and the wall of the sheath encircling it, but the device may be slid along the slot by finger pressure on the upstanding arms to spread the slot. The clamp need not be contilevered to accommodate a locking sleeve but can be cut from a plastic extrusion in any length desired. No air can reach the incision but the device can still be easily slid along the slot, finger pressure on the arms and slot preventing the device from popping out of the slot. The Introducer remains protected in the sheath at all times.

BRIEF DESCRIPTION OF THE DRAWING

FIG. 7 is a view similar to FIG. 1 of another embodiment of the invention in which both catheter and covering sheath are received in the slot of the clamp.

FIG. 8 is an enlarged end elevation, in section on line 8—8 of FIG. 7 showing the clamp closed on both catheter and sheath;

FIG. 9 is a view similar to FIG. 8 showing finger pressure releasing the catheter and sheath to permit sliding of the catheter.

FIG. 10 is an enlarged side elevational view showing the distal end of the indwelling device, covering sheath and the apparatus to which the device is attached;

FIG. 11 is an enlarged side elevational view of the self-supporting transparent bell shaped dome covering the incision;

DESCRIPTION OF A PREFERRED EMBODIMENT

Figure 1:
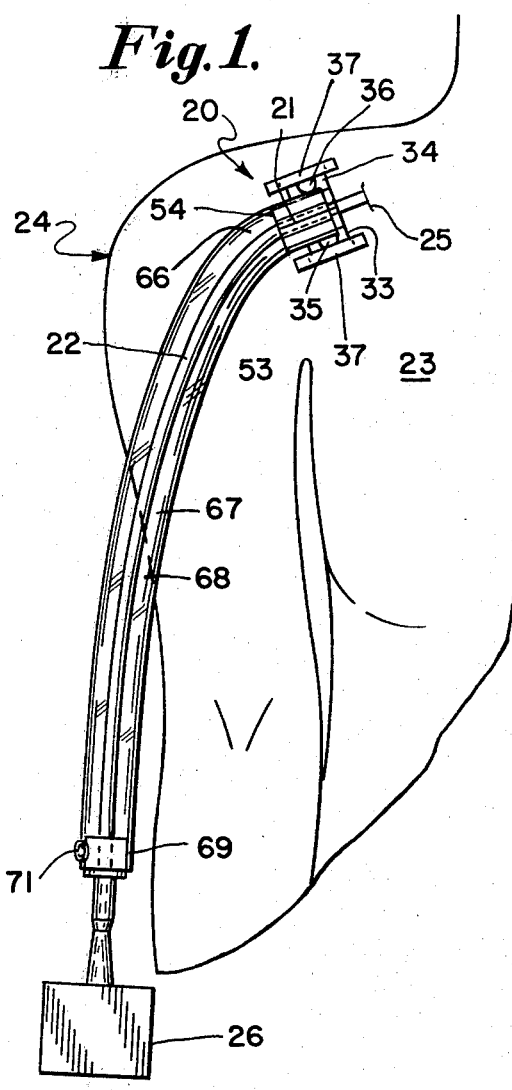
FIG. 1 is a fragmentary front elevation of a portion of the human body with a clamp of the invention in place.

As shown in FIGS. 1-5, the catheter clamp 20 of the invention, is used to anchor, or fasten, a length 21 of an indwelling device such as a catheter, tube or lead 22 to the skin 23 of a patient 24, at or near the incision 25 so that the tip of the catheter within the body of the patient will remain in exactly the desired location without axial advance or retraction.

The element 22 may be the lead of a pacemaker unit, the tip being in the heart of the patient 24 and the lead being connected to a source of power, or generator 26 outside the incision 25 as shown.

Figure 2:
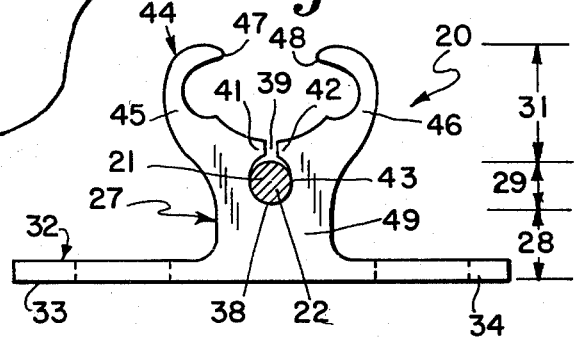
FIG. 2 is an enlarged end elevation of the clamp with a catheter in the groove, and freely slidable therein.
Figure 3:
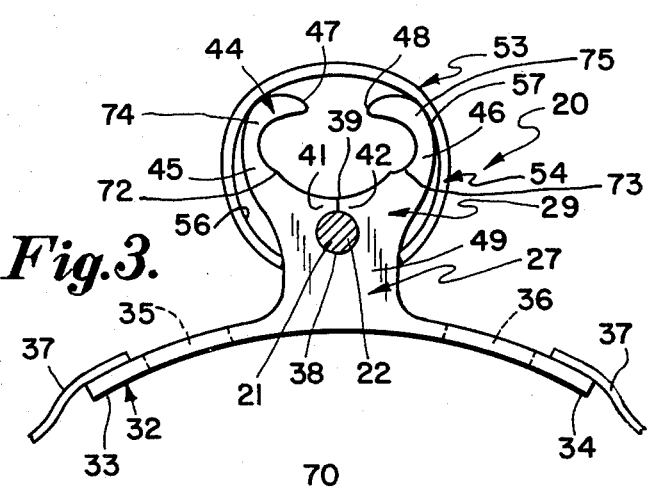
FIG. 3 is a view similar to FIG. 2 showing the locking sleeve tightening the walls of the slot to lock the catheter.

The catheter clamp 20 includes a block, or body 27 of soft, flexible resilient material such as plastic, the body 27 preferably being elongated and having a lower portion 28, a central portion 29, and an upper portion 31 (FIG. 2).

The lower portion 28 of body 27, comprises integral base flange means 32, preferably including a pair of oppositely extending ears 33 and 34, having holes 35 or 36 to permit attachment by sutures proximate the incision 25. Preferably, however, the clamp 20 is attached to the skin 23 by adhesive tape 37 passed over the flange ears 33 and 34.

The central portion 29 of the elongated block 27 includes an open elongated catheter slot 38, of nearly circular cross section, having an upward opening slit 39, with opposite walls 41 and 42 which are normally spaced apart. The slot 38 has a nearly cylindrical inner wall 43 normally of greater inside diameter than the outside diameter of the catheter 22 with which the clamp is used, so that the catheter 22 is normally freely slidable therein for advance or retraction, as shown in FIG. 2.

The upper portion 31 of block 27 comprises upstanding clamp jaw means 44 which includes a pair of arms 45 and 46, each upstanding from the common central portion 29, on an opposite side of the catheter slot 38, and each having a tip 47 or 48 normally spaced from the other and extending in parallelism longitudinally of the block.

The clamp jaw means 44 in the upper portion 31 and the common central portion 29 are integrally connected to the base flange means of the lower portion 28 of the block 27 by an integral web 49 which is preferably not full length of the block, but instead, extends from the front edge 51 only a short distance toward the rear edge 52 of the block so that the central and upper portions are cantilevered relative to the base flange of the lower portion.

The clamp 20 includes external locking means 53, separate from the block 27, and preferably in the form of a hollow, tubular sleeve 54 of flexible, resilient transparent plastic 55. The hollow tubular sleeve 54 is substantially equal in length to the length of the upper portion 31 and central portion 29 of block 27, and has an inner face 56 of predetermined diameter, or dimensions, to slidably fit endwise over the outer face 57 of the upstanding arms 45 and 46 of the clamp jaw means 44 and deform the arms toward each other to thereby reduce the diameter of the slot 38 and cause it to lock on, and firmly grip, the length 21 of the catheter 22 therein. A recess 58 in the forward peripheral rim 59 of sleeve 54 fits around the integral web 49 of block 27 so that substantially the entire block is covered where it may be contacted by the fingers of the surgeon.

Figure 6:
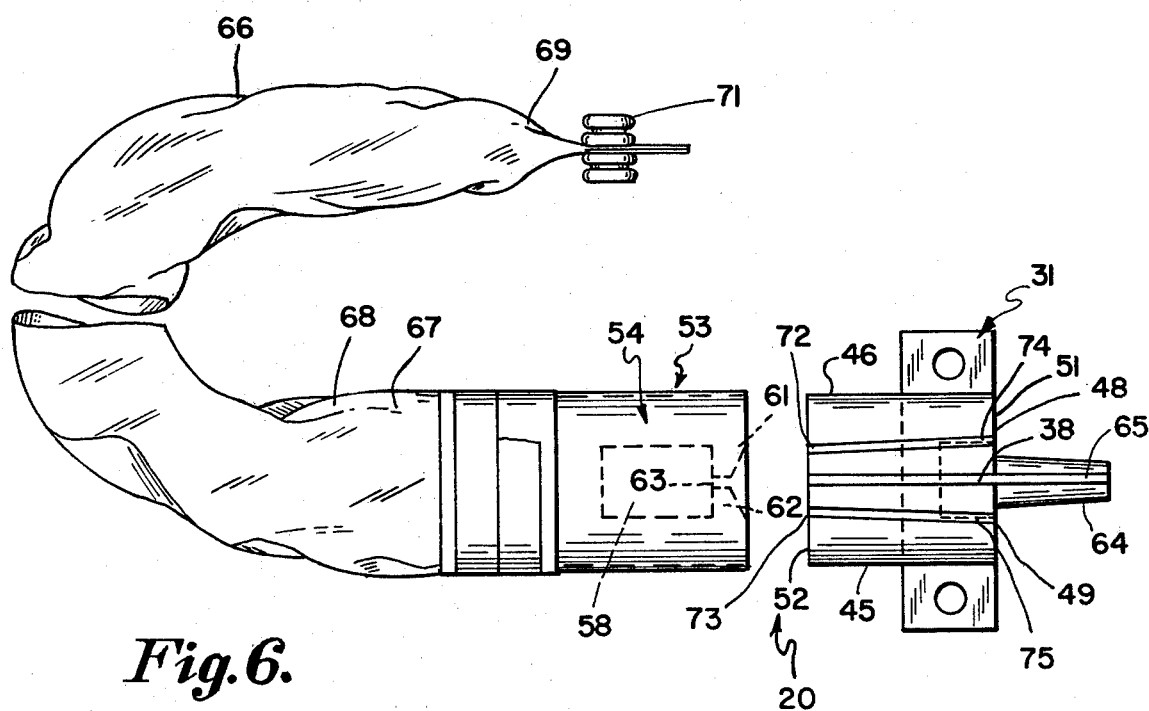
FIG. 6 is a top plan view on a reduced scale showing a clamp of the invention with an integral tapered slotted nose and another form of external locking sleeve.

As shown in FIG. 6 the recess 58 may not only slide over the web 49 but the sleeve 54 may have a pair of tongues 61 and 62 defining a narrow slit 63, the slit 63 spreading to receive the web 49 and then closing in front thereof to protect the front edge of the block from contamination.

Preferably, also, as shown in the embodiment of FIG. 6, the block 27 includes an integral tapered nose 64, of predetermined dimensions, to slidably fit within the corresponding female recess in an introducer, or trocar, there being a catheter slot 65, in extension of slot 38 in the forwardly projecting nose. The nose 64 seals the trocar against leakage of blood. The inside diameter of the extension slot 65 differs from the inside diameter of the slot 38 so that the catheter will slide freely in the slot 65 when the nose 64 is in the trocar recess but the external locking means 53 has been removed from the block 27 to permit ready slidable advance or retraction of the catheter, or when the sleeve 54 has been pressed as in FIG. 4.

Figure 5:
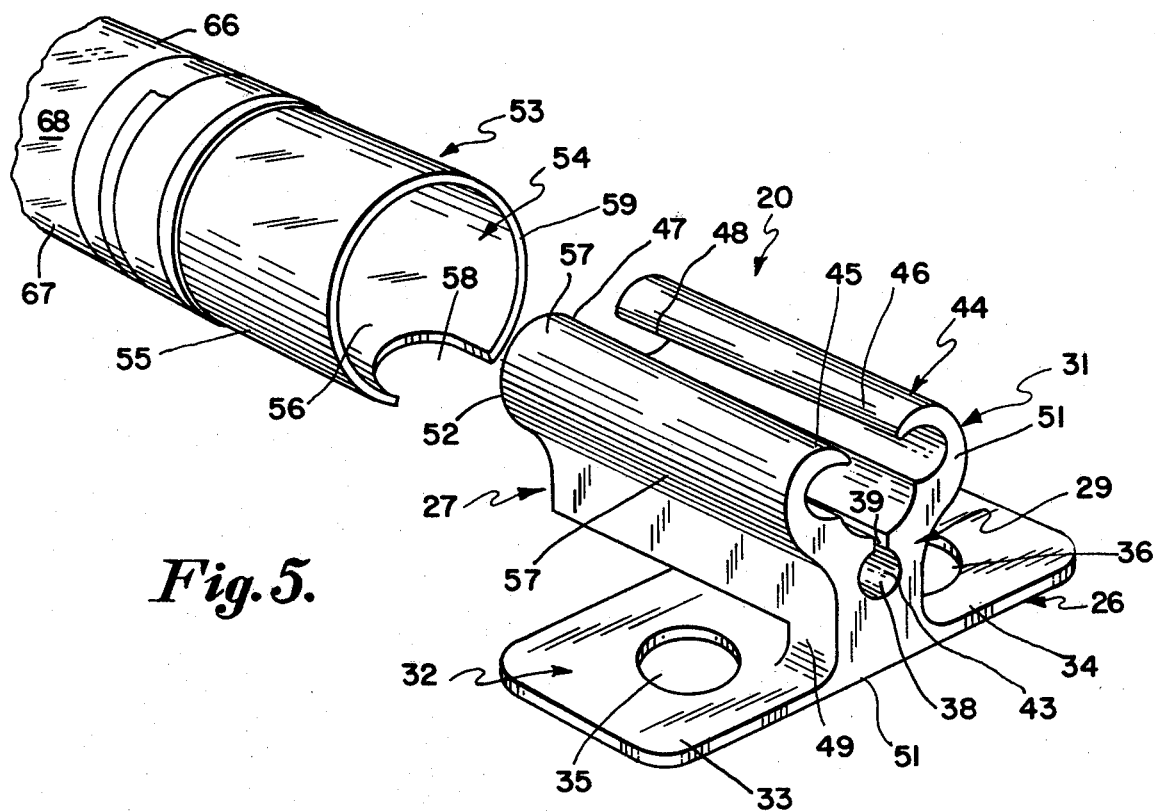
FIG. 5 is an enlarged perspective view of a clamp of the invention, the external locking sleeve and a portion of the sheath attached around the sleeve.

Preferably the hollow tubular sleeve 54 has one end 66 of an elongated hollow tubular sheath 67 of impervious plastic material 68 adhered permanently in sealing engagement therearound as shown in FIGS. 1, 5, and 6 the catheter 22 thus being enclosed therein for its full length to the other end 69. The end 69 is closed by snap fasteners 71 proximate the power source 26 so that the catheter 22 is completely protected from human touch or from contamination from the incision, skin, or the ambient atmosphere.

The catheter clamp of the invention can be fastened and released by the finger 70 of the surgeon applied from outside the sheath 67 and outside the locking sleeve 54 by sliding the sleeve 54 endwise on and off the clamping jaw means 44 of the block 27, while they remain within the sheath, and then slidably advancing or retracting the catheter 22, in slot 38.

Figure 4:
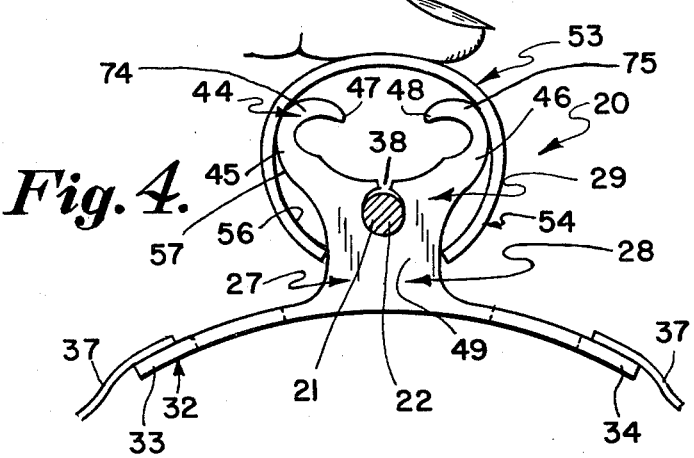
FIG. 4 is a veiw similar to FIG. 1 and FIG. 2 showing that finger pressure spreads the clamp arms and increases the diameter of the slot to freely slide the catheter.

This is because the arms 45 and 46 each flare outwardly away from each other at 72 and 73 and are then bent inwardly at 74 and 75 toward each other proximate the tips 47 and 48. By this special configuration, which I call a rhomboid or parallelogram structure, the gentle pressure of one finger 70 of the surgeon applied to the tips 47 and 48 in the direction of the catheter slot 38, causes the slot to widen and increase in diameter for free slidability of the catheter as shown in FIG. 4. Thus, the locking means 53 need not be removed once in place, but only slightly compressed to enable slidable adjustment of the catheter and instant locking thereof upon release of the finger pressure.

As shown in FIGS. 7 to 12 in the preferred embodiment of the sterile assembly of the invention the clamp 76, corresponding to clamp 20, instead of being inside the tubular flexible covering sheath of transparent plastic 67 is outside the indwelling device 77, such as a catheter, and outside the sheath 67. The elongated, catheter slot 78, in clamp 76 is normally of such dimension that it will receive both the catheter 77 and a layer of its covering sheath 67 in the slot and lock the catheter against forward or rearward sliding movement relative to the clamp. The clamp is affixed to the skin of the patient by its integral flange 79, corresponding to flange means 32, and adhesive tape 37 but, in this embodiment, the clamp 76 need not be close to the incision 25 in the patient.

Because clamp 76 is outside the sheath and is normally closed on both catheter and its sheath, the external locking means 53 comprising sleeve 54, and the recess 58 in the sleeve rim, of the embodiment of FIGS. 1-6 are not necessary and clamp 76 can be cut in any desired length from a single extrusion of uniform cross section.

To keep the incision 25 and indwelling device 77, free of contamination with the air the sheath 67 is provided with an elongated, bell shaped, dome 81, of self-supporting, preferably transparent plastic 82 having a base flange 83 with a skin contacting surface 84 of soft material or structure 85 covered by a layer of adhesive 86, the adhesive normally being covered by a strippable masking sheet 87. The proximal end 66 of flexible, impervious plastic sheath 67 is adhered around the neck 88 of dome 81, the dome keeping wrinkles of the sheath material away from the incision 25.

It will be seen that the incision can be made while the indwelling device 77 is loosely, but completely, enclosed within the sheath 67, whereupon the dome 81 is adhered to the skin around the incision and the clamp 76 affixed to the skin at a distance from the incision with device 77 and the adjacent thin wall 89 of the sheath securely clamped in the slot 78.

The elongated, protective covering, tubular sheath 67 of flexible, transparent, impervious plastic 55, with its sterile interior, extends the full length of the indwelling device 77, from its integral dome of self-supporting, wrinkle free, memory plastic 82 (such as vinyl or latex) at the proximal end 66, covering the incision 25, co-extensively in length with device 77 and loosely sleeved therearound to its distal end 69 where it is sealed around the distal end 91 of the device 77 proximate the generator 26, or other apparatus connected to the indwelling device.

As best shown in FIG. 10, the indwelling device 77 is preferably provided with an enlargement, or nub 92 near its distal end 91 serving as a male member slidably fitting and sealing within a female socket 93 formed of the self-supporting plastic 96, the distal end 69 of the tubular sheath being affixed therearound by adhesive 86. An outward flare 94 in socket 93 assists in the engagement and disengagement of the nub 92 in the socket.

As shown in FIG. 9 pressure of the finger 70 of the surgeon, opens the slot 78 to free the indwelling device and the adjacent thin wall 89 of the sheath 67 from the resilient grip of the clamp whereupon the surgeon can slide the indwelling device 77 to a new position with the incision or retract it all without human hands touching the device 77 and without any contamination of the incision 25. The finger 70 while releasing the grip of the clamp on the catheter or lead, completes a loop around it, so that the device cannot pop out of the slot.

Figure 12:
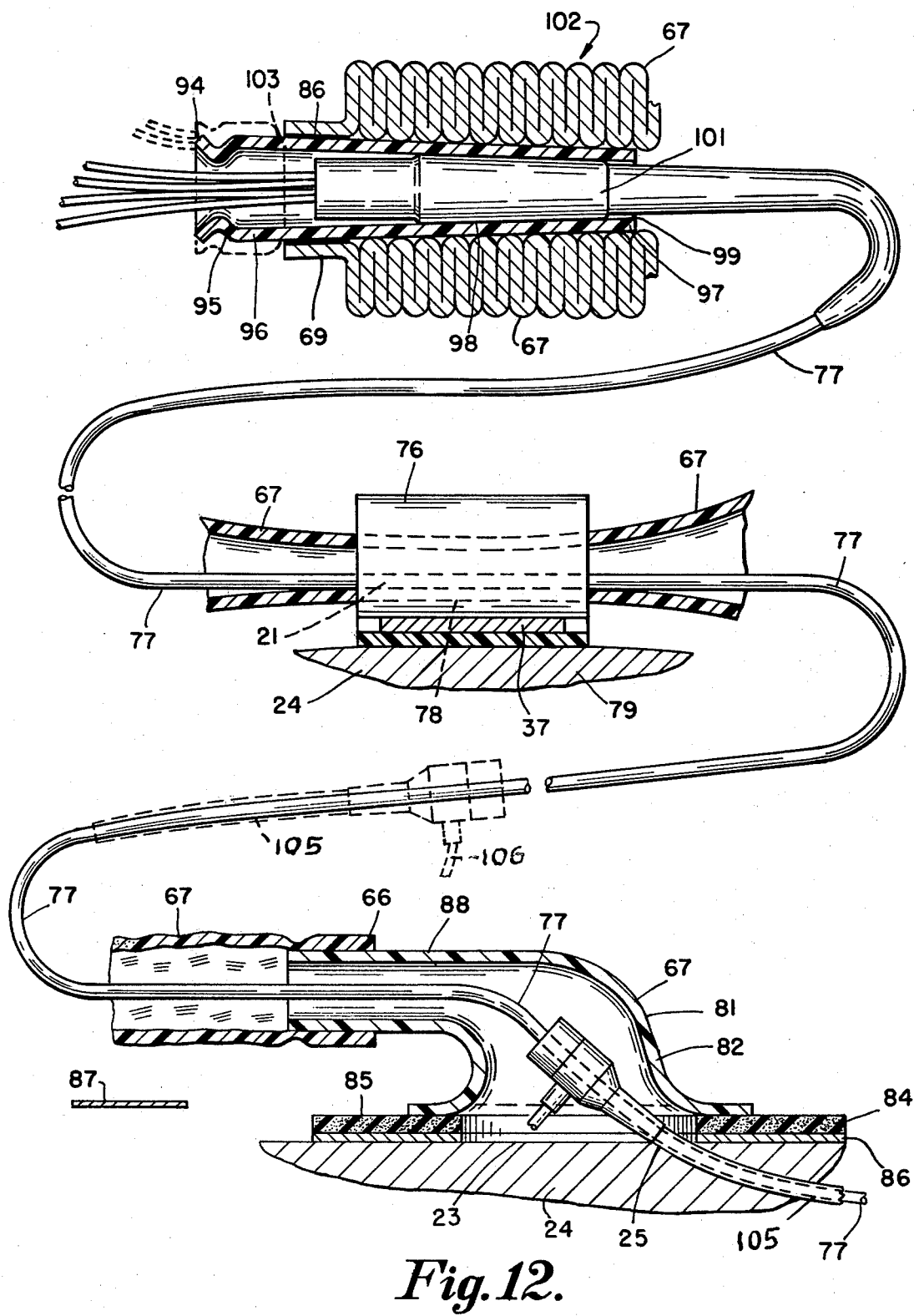
FIG. 12 is a view similar to FIG. 6 of the preferred embodiment of the sterile protective and fastening assembly of the invention.

As shown in FIG. 12, because the nubs of the indwelling devices 77 of various manufacturers vary in configuration and dimensions, it is preferred that the socket 97 be an elongated tube of self-supporting plastic 96 about four inches long, having an inward-projecting annular flange 95 of predetermined reduced diameter just within the outward flare 94 and a tapered axial bore 98 tapering to a reduced diameter at 99. Thus, an elongated nub 101 may be snapped through the flange 95 and wedged into the tapered bore 98 for a sealing fit, as can nubs of other dimensions. The elongated socket 97 permits the sheath 67 to be shipped compressed into accordian type configuration as shown at 102 on the socket ready to be drawn forwardly over the indwelling device 77 up to the incision, when in use. The plastic 96 of socket 97 is readily deformable so that it can be distorted to fit around nubs 101 of oval, circular, or cubical cross section. As shown in dotted lines a nub 103, of larger dimensions than nub 101 will wedge in an outer portion of the tapered axial bore 98.

The Introducer 105 is shown in full lines in the incision 25 in FIG. 12, and is of the type having a side arm 106. The conduit 107 from the side arm is sealable between the skin 23 and the adhesive layer 86, the soft layer 85 being compressed but the seal maintained. The Introducer may be slid back to the position shown in dotted lines when no longer needed while still sealed within the sheath.

I claim:

1. A sterile assembly for protecting an elongated indwelling device having a proximal end, for insertion in an incision in the human body, and a distal end, for connection to a medical device outside the human body, said assembly comprising:

an elongated, tubular sheath of sterile, impervious, limp, flexible, plastic substantially co-extensive in length with said indwelling device and having a proximal end and a distal end;

an elongated, bell shaped dome of self-supporting plastic sealingly affixed to the proximal end of said sheath: said dome being shaped and dimensioned to cover said incision and keep the incision and indwelling device free of contamination with air and having an annular base flange with a skin contacting surface covered by a layer of adhesive adapted to be affixed around said incision, said surface normally covered by a removable strippable sheet and a hollow support tube of said self-supporting plastic, and of predetermined length, sealingly connected to the distal end of said sheath, said tube having an axial bore which tapers from its outer end in a progressively reduced diameter to its inner end for slidably fitting and sealing the conventional nub on said indwelling device.

2. A sterile assembly as specified in claim 1 wherein: said hollow support tube is several inches in length and said sheath is compressed into accordian folds onto said tube for storage and shipment.

3. A sterile assembly as specified in claim 1 wherein: said hollow support tube includes an outwardly flared flange at its outer end for guiding an indwelling device being inserted therein.

4. A sterile assembly as specified in claim 1 wherein: said hollow support tube includes an inwardly projecting, annular portion of reduced diameter proximate its outer end for snap fitting over the enlarged nub of an indwelling device.

5. A sterile assembly as specified in claim 1 plus:

a clamp of soft, resilient plastic material having a base flange for affixation to the skin of said human body;

a pair of clamp arms upstanding from said base flange and an elongated clamp slot located between said base flange and said clamp arms;

said clamp slot receiving and gripping a length of said indwelling device and a corresponding length of the said sheath enclosing the same to affix the same at a predetermined location relative to said incision but releasing said indwelling device for slidable adjustment when said clamp arms are actuated.

6. A sterile assembly as specified in claim 5 wherein:

said clamp is of uniform cross sectional shape and dimension throughout it's length whereby a plurality of identical said clamps can be cut from a single plastic extrusion.

7. A sterile assembly as specified in claim 1 wherein:

said bell shaped dome is of wrinkle free, clear, transparent plastic to enable said incision to be viewed when said base flange is adhered around said incision.

8. A sterile indwelling device assembly comprising:

an indwelling device of predetermined length and diameter having a proximal end and a distal end;

a tubular sheath of impervious, flexible, transparent plastic enclosing said device for substantially the full length thereof, said sheath having thin, limp walls, a proximal end with an elongated, bell shaped dome of self-supporting, plastic adhered thereon for sealing around an incision and a distal end sealed around the distal end of said device;

clamp means including base flange means for affixation to the skin at a spaced distance from said incision and clamp jaw means of soft resilient material having a pair of clamp arms upstanding from said base flange means and an elongated, clamp slot located between said base flange means and said clamp jaw means;

said slot receiving a length of said indwelling device, and the portion of said sheath enclosing said length, therewithin and clamping or unclamping the same against longitudinal movement therealong in response to application, or release of finger pressure on said upstanding clamp arms.

9. A sterile indwelling device assembly as specified in claim 6 wherein:

said distal end of said sheath included an elongated, hollow tube of self-supporting plastic having an annular, inward projecting flange at its distal end and having an axial bore tapering from said flange to an opposite end of reduced diameter for wedge sealing therein, a nub at the distal end of said indwelling device.

10. In combination:

an indwelling device, such as an elongated electrode, or catheter, of predetermined length and predetermined, uniform outside diameter;

a clamp for said device, said clamp comprising an elongated block of flexible, resilient material having a pair of longitudinally extending, laterally spaced apart, clamp arms upstanding therefrom and defining an elongated slot therebetween for receiving a length of said indwelling device, said clamp having an integral outwardly protruding flexible base flange for attachment thereof to the skin;

and an elongated, protective, covering, tubular sheath of flexible, transparent impervious plastic having thin walls and substantially co-extensive in length with the length of sais indwelling device, said tubular sheath having an elongated bell shaped dome of self-supporting transparent plastic fixed at its proximal end for enclosing and sealing the area around an incision, said sheath being sleeved around said indwelling device throughout its length and being sealed at its distal end to the distal end of said device;

said clamp slot being of predetermined diameter equal to, or less than, the outside diameter of said indwelling device plus the thickness of the wall of said tubular sheath, to normally lock said sheathed device against sliding in said slot except when pressure is exerted on said upstanding arms to open said slot for sliding of said device therealong.

11. The method of positioning an indwelling device relative to an incision in the skin of the human body, by means of a releasable clamp affixable to said skin, while maintaining sterility of said device, which comprises the steps of:

entirely covering said indwelling device with a tubular sheath of flexible sterile, impervious transparent plastic from the area of said incision to proximate the end of said device;

adhering the end of said sheath, at said incision, around said incision and sealing the other end thereof around said device to seal said device against contamination by air;

then gripping a length of said device, and the corresponding length of said sheath encircling the same against longitudinal movement in said clamp; and then affixing said clamp to said skin at a selected spaced distance from said incision, to prevent longitudinal movement of said device.

* * * * *

UNITED STATES PATENT OFFICE
CERTIFICATE OF CORRECTION

Patent No. 4,392,853            Dated July 12, 1983

Inventor(s) Rudolph Muto

It is certified that error appears in the above-identified patent and that said Letters Patent are hereby corrected as shown below:

Col. 7, Claim 9, line 2 "claim 6 wherein:"

should read "claim 8 wherein:"

Signed and Sealed this

Thirteenth Day of September 1983

[SEAL]

Attest:

GERALD J. MOSSINGHOFF

Attesting Officer      Commissioner of Patents and Trademarks